United States Patent [19]

Ellman

[11] 4,428,375
[45] Jan. 31, 1984

[54] SURGICAL BAG FOR SPLENORRHAPHY

[76] Inventor: Barry R. Ellman, 254 Stratton Rd., Rutland, Vt. 05701

[21] Appl. No.: 348,976

[22] Filed: Feb. 16, 1982

[51] Int. Cl.³ .............................................. A61B 17/12
[52] U.S. Cl. ............................ 128/334 R; 128/303 R; 128/325
[58] Field of Search ................. 128/1 R, 303 R, 325, 128/334, 335.5

[56] References Cited

U.S. PATENT DOCUMENTS

| 2,143,910 | 1/1939 | Didusch | 128/335.5 |
| 3,983,863 | 10/1976 | Janke et al. | 128/1 R |
| 4,217,890 | 8/1980 | Owens | 128/303 R |

OTHER PUBLICATIONS

De Mueles et al.–Annals of Thoracic Surgery–vol. 16, No. 2, Aug. 1973, pp. 199–200.
Lahey Intestinal Bag–1959 Daud Rubber Co. Catalogue, p. 24.
Buntain et al., Surgery, Nov. 1979, pp. 748–760.

Primary Examiner—Dalton L. Truluck

[57] ABSTRACT

A surgical net bag for encapsulating a fractured organ during surgical repair. The bag is provided with multiple drawstrings to aid in conforming the bag to the organ for applying thereto substantially uniform pressure to obtain hemostasis. The bag is especially useful for surgical repair of fractured spleens.

5 Claims, 4 Drawing Figures

SURGICAL BAG FOR SPLENORRHAPHY

This invention relates to a surgical bag for encapsulating an organ during surgical repair, and in particular a surgical bag for use in a splenorrhaphy procedure (a surgical procedure for repairing fractured spleens, as distinguished from removing them).

BACKGROUND OF THE INVENTION

The medical journal Surgery, Vol. 86, Nov. 5, November 1979, pages 748–760, whose contents are hereby incorporated by reference, is a review article summarizing the state of the art in splenorrhaphy, the surgical repair of traumitized spleens. As explained in this article, the spleen is a friable vascular organ, and when injured typically suffers transverse rupture or fracture. Repair by suturing the tissue is complicated by its lack of tensile strength. Various procedures have been devised which are reported on and illustrated in this article, extending from the use of fine sutures in different patterns, to the use of absorbable suture ladders which are sutured to the organ across the fracture. Such known procedures are complicated, difficult to carry out during profuse bleeding, do not readily provide hemostasis, and are time consuming.

BRIEF SUMMARY OF INVENTION

The chief object of the present invention is a new surgical procedure for repairing fractured organs that is simpler and less time-consuming, can be carried out during profuse bleeding at the fracture, and is effective in closing the fracture to control bleeding and maintaining it closed during subsequent healing.

A further object of the invention is an improved splenorrhaphy procedure.

Still another object of the invention is a novel surgical bag for use during surgical repair of a fractured organ.

These and further objects and advantages of the invention as will appear hereafter are achieved, briefly speaking, with a novel surgical bag of flexible mesh or network construction whose threads or solid parts are composed of patient absorbable or tolerable material. The bag, which is elongated, has one end closed and the opposite end open to receive the fractured organ to be repaired. The open end of the bag has at least one drawstring, preferably two or more, threaded through the mesh openings at the bag open end. During the surgical procedure, the surgeon places the fractured organ into the bag in such manner that its vascular connections extend through the open end. Next, the surgeon pulls the drawstrings snug so as to cause the mesh bag walls to conform to the organ shape and compress the organ sufficiently to close any fractures therein and provide hemostasis. The drawstrings are then tied, and the surgeon proceeds to suture across the wound, passing the suture needle and suture through the mesh openings to reinforce the typically weak tissue and prevent the sutures from pulling out of the tissue. The bag remains in place sutured to the organ after closing of the patient and during the healing process.

The above described procedure is especially useful for repair of fractured spleens because of the location of the vascular connections and the irregular shape of the spleen, as tightening of the bag is effective in closing of the wound and hemostasis.

The invention will now be described in greater detail with respect to a preferred embodiment thereof, reference being had to the annexed drawings.

DETAILED DESCRIPTION OF PREFERRED EMBODIMENT

Figure 1:
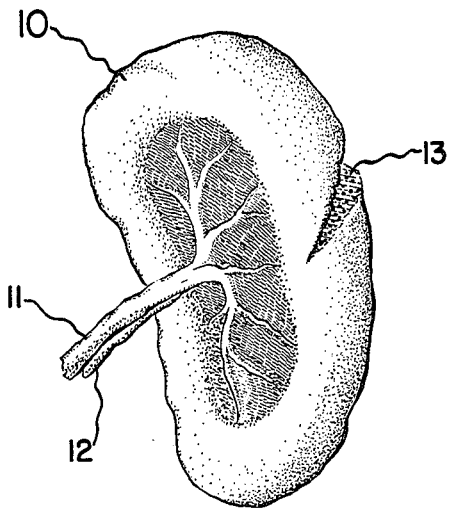
FIG. 1 schematically illustrates a fractured spleen.

Referring now to the drawings, FIG. 1 is a schematic view of a spleen viewed from the standpoint of a surgeon when exposed in the patient's body in the course of surgery. The spleen comprises a main, irregularly-shaped, body part 10 unconnected to the patient's body except by way of its vascular connections, specifically an artery 11 and vein 12. When damaged, the spleen 10 frequently fractures, as depicted at 13. As mentioned above, because the spleen tissue is friable, it is difficult to suture across the fracture to close same while retaining the sutures to allow the wound to heal, which it does quickly because of the ample blood supply.

Figure 2:
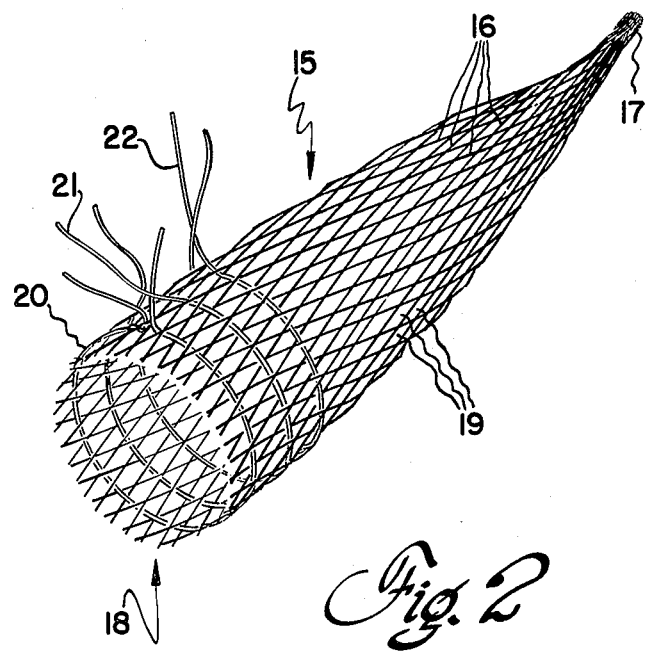
FIG. 2 is a plan view of one form of surgical bag for splenorrhaphy in accordance with the invention.

A feature of my invention is to make available to the surgeon a pliable or flexible bag 15, illustrated in FIG. 2. The bag 15 has a mesh or network construction, and is made up of threads or solid parts 16 of inert materials that the patient can tolerate or will be absorbed by the body. Such non-metallic, inert, pliable surgical materials are well known in the art and may be, for example, of synthetic materials, such as polyproylene, nylon, silicone or polyethylene, e.g., DACRON or TEFLON, or of natural materials, such as catgut. One end of the bag 15 at 17 is closed. The opposite end 18 is left open. Through the mesh openings 19 adjacent the open end 18 are passed three longitudinally-spaced drawstrings 20, 21, 22 so as to encircle the open end 18. The drawstrings 20, 21, 22 are composed of surgical material similar to that employed for the bag strands.

Though the bag 15 can be made up of woven or knitted strands, I much prefer that the bag is not woven or knitted but is formed as one piece of thin sheet material with thin sheet walls or threads 16 having openings 19. This is readily accomplished by, for example, extrusion. Preferably, the sheet is about 1 mm or less thick, and the holes are 3–9 mm in size with center-to-center spacing of about 4–10 mm, though other dimensions can also be used. As an alternative, use can preferably be made of mesh-type bags, as illustrated in the drawings, of a type readily commercially available for packaging groceries and the like, but made up using surgical material strands. Such bags typically are made up of crossing strands, joined as by sealing at the crossings, and with the strands bundled and joined together to form the closed end 17. Such a bag conforms well to the irregular outline of the spleen when the drawstrings are pulled taut, and will be inexpensive to manufacture. The strands typically would have a diameter of 0.25 mm. Preferably, the bag 15 has an overall length of about 7–15 cm, a 5 cm diameter, expandable to about 9 cm, with the drawstrings spaced about 1 cm in from the open end and from each other. These dimensions would be suitable for a human spleen, or for other animals. For other organs, different dimensions can be chosen in the light of the teachings given herein.

Figure 3:
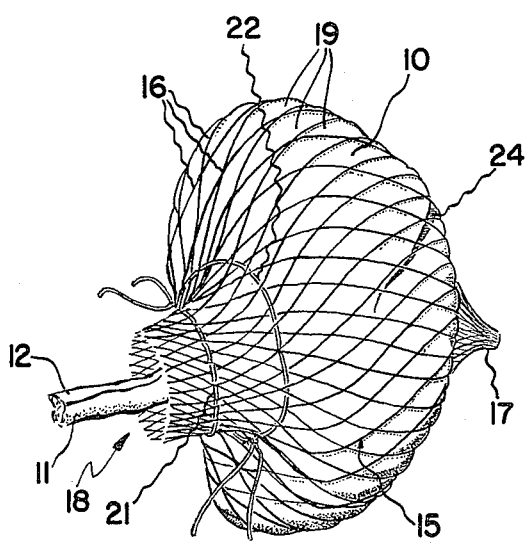
FIG. 3 shows schematically the organ of FIG. 1 within the bag of FIG. 2 with two of its drawstrings tied.
Figure 4:
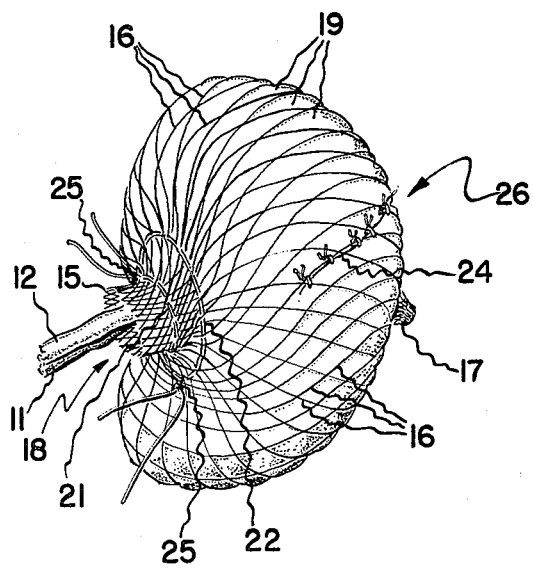
FIG. 4 shows schematically a later stage in the surgical procedure with the bag sutured to the repaired area of the spleen.

During a splenorrhaphy procedure, the surgeon lifts up the spleen and inserts it into the bag 15, through its open end 18. As will be observed in FIG. 3, the entire spleen will fit within the expanded, flexible bag except for the connecting blood vessels 11, 12. Next, the surgeon pulls snug one or more of the drawstrings 21, 22 so as to cause the mesh walls 16 to adjustably conform to the organ shape and apply gradually increased uniform pressure on the organ 10 until the wound 13 closes, shown at 24, and hemostasis is obtained. Then, the surgeon ties off the drawstrings 21, 22, as shown at 25. The third drawsting 20 was removed as unnecessary for this sized organ. With hemostasis being obtained by reason of the wound-closing pressure applied by the encapsulating bag 15, the surgeon can proceed to suture across the wound. The sutures 26 are extended through the mesh openings 19 adjacent the wound so that they wrap around the mesh threads 16, and are thus prevented from pulling out of the friable spleen tissue. This is illustrated in FIG. 4, with the suturing being schematically depicted at 26. As will be observed, the suturing is across the closed wound 24 and through the overlying bag meshes. After suturing is completed, the patient is closed with of course the bag 15 remaining attached to the spleen.

One of the features of the invention is that the mesh bag is composed of flexible, conformable material which substantially completely encloses or encapsulates the living organ. When the drawstrings are tightened, the bag network will conform to the irregularly-shaped organ structure and will impart substantially uniform compression to substantially all surfaces of that stucture. This uniform pressure is the key to hemostasis without damaging the organ by excessive pressure. The multiple drawstrings on the bag allow the surgeon to selectively or adjustably tighten the bag so as to apply this uniform pressure around the organ. This feature also allows greater flexibility in sizing one bag to accomodate organs of different size, but in addition, and of equal importance, allows the surgeon to gradually increase the uniform pressure on the organ until the proper minimal pressure is reached to obtain hemostasis, at which time the drawstrings can be tied. Hemostasis without injury to the fractured organ due to excess pressure is a principal advantage of the net bag of the invention.

Another important advantage is that the suturing of the bag to the organ joins the bag to the repaired area, reinforces the sutures and prevents suture separation from the organ, especially with a friable organ such as the spleen.

Still another advantage is that the multiple interstices or openings in the net allows ingrowth of tissue through the net openings and around the net solid parts and thus enhances healing. The use of absorbable or patient tolerable material for the bag material contributes to achieving this advantage.

FIG. 4 illustrates the situation after the tied bag has been sutured to the organ and the wound closed. This figure also illustrates how the bag closely conforms to the irregularly-shaped organ, with only the blood vessels 11, 12, around which the bag neck is secured, protruding. The one-piece bag construction significantly contributes not only to the low cost of manufacturing the bag, but also to the uniform pressure applying and conforming features of the invention.

While the novel bag of the invention is especially suited for repairing fractured spleens, it may also be used with other living tissue which has essentially one end connected to the body and which can be lifted and inserted within the net bag and the bag open end then tied around the connecting blood vessels.

While my invention has been described in connection with specific embodiments thereof, those skilled in the art will recognize that various modifications are possible within the principles enunciated herein and thus the present invention is not to be limited to the specific embodiments disclosed.

What is claimed is:

1. A surgical bag for enclosing an organ during surgical repair, comprising a generally tubular flexible bag having one end closed and the opposite end open, said bag having an open net construction and being made of mesh type material constructed of patient tolerable or absorbable threads and sized to allow the organ to be placed within the bag through its open end, and plural drawstrings of patient tolerable or absorbable material strung through the net adjacent and spaced at different distances from the bag open end and capable when pulled to conform the bag tightly around the organ in such manner as to close any fractures therein.

2. A surgical procedure comprising the steps:
   (a) placing a fractured living organ to be repaired within a net bag constructed of patient tolerable or absorbable strands, said bag having one end closed and the opposite end open to receive the organ with its vascular connections extending out through the bag open end, said bag having plural spaced drawstrings adjacent its open end and threaded through the net strands around its open end,
   (b) selectively pulling and tieing the drawstrings snub around the vascular connections and the organ such that the bag substantially uniformly compresses the organ pressing shut any fractures therein to obtain hemostasis, and
   (c) suturing closed the organ fracture around the net strands and net openings to reinforce and support the suture closure of the fracture, said bag remaining attached to the organ upon completion of the procedure.

3. A surgical procedure as claimed in claim 2, wherein the bag is made of mesh type material, and the plural drawstrings are strung through the net spaced at different distances from the bag open end.

4. A surgical procedure as claimed in claim 3, wherein the bag is elongated and three spaced drawstrings are provided at the bag open end.

5. A surgical procedure as claimed in claim 3, wherein the procedure is a splenorrhaphy, and the organ is a spleen.

6. A surgical bag as claimed in claim 1 wherein the bag has an overall length of about 7–15 cm, a diameter of 5 cm expandable to about 9 cm, and with the drawstrings spaced about 1 cm apart.

* * * * *